United States Patent [19]
Fitzgerald et al.

[11] Patent Number: 5,317,908
[45] Date of Patent: Jun. 7, 1994

[54] HIGH VISCOSITY TRANSDUCER FOR VIBRATORY VISCOMETER

[75] Inventors: John V. Fitzgerald, Metuchen; Frank J. Matusik, Piscataway, both of N.J.; John L. Batton, New York, N.Y.

[73] Assignee: National Metal Refining Company, Inc., Metuchen, N.J.

[21] Appl. No.: 874,821

[22] Filed: Apr. 28, 1992

[51] Int. Cl.$^5$ .......................................... G01N 11/06
[52] U.S. Cl. .................. 73/54.26; 73/54.25
[58] Field of Search ............... 73/54.24, 54.25, 54.26, 73/54.27, 54.28, 54.29, 54.35, 54.02

[56] References Cited

U.S. PATENT DOCUMENTS

| | | | |
|---|---|---|---|
| 3,382,706 | 5/1968 | Fitzgerald | 73/54.25 |
| 4,488,427 | 12/1984 | Matusik et al. | 73/54.26 |
| 4,566,188 | 1/1986 | Matusik et al. | 73/54.25 |
| 4,754,640 | 7/1988 | Fitzgerald et al. | 73/54.25 |
| 5,054,313 | 10/1991 | Fitzgerald et al. | 73/54.27 |

Primary Examiner—Hezron E. Williams
Assistant Examiner—Michael Brock
Attorney, Agent, or Firm—Arthur L. Lessler

[57] ABSTRACT

A transducer for inline process control of highly viscous fluids at high pressure and high temperature having a torsionally oscillating sensor tip supported by a pressure resistant threaded body portion. The sensor tip, which includes a thermocouple to measure fluid temperature, is driven by a crossarm which oscillates with a constant angular amplitude, the power required to maintain that amplitude despite the viscous resistance offered by the fluid being a measure of the viscosity-density product of the fluid. The crossarm driver and detector electromagnetic coils are oriented at right angles to each other to reduce crosstalk and transducer housing diameter. The associated electronic control unit includes means to compensate for the effects of fluid flow rate and fluid pressure which were found to be encountered with the vibratory viscometer method of measurement when inline measurements are made on high viscosity fluids.

15 Claims, 8 Drawing Sheets

HIGH VISCOSITY TRANSDUCER FOR VIBRATORY VISCOMETER

BACKGROUND OF THE INVENTION

This invention relates to a rotational vibratory viscometer for measuring viscosity of fluids at high temperature and high pressure; and is especially suited for, but not limited to, measuring the viscosity of high viscosity fluids such as molten polymers and bread dough.

Rotational vibratory viscometers are well known in the art, and generally comprise (i) a transducer having a tip immersible in a fluid the viscosity of which is to be determined, (ii) an electromagnetic drive coil for causing the tip to rotationally oscillate with a very small angular amplitude, (iii) a feedback control circuit for maintaining the angular amplitude of oscillation of the tip at a predetermined constant value irrespective of the viscosity of the fluid, and (iv) a circuit for determining the power supplied to the drive coil, usually by squaring the current supplied to said coil, which power is a measure of the viscosity of the fluid.

A viscometer of this type is described, for example, in "Viscometer for Energy Saving", J. V. Fitzgerald, F. J. Matusik and P. C. Scarna, Jr., Measurements & Control, April 1980 and in "Continuous Viscosity Control Improves Quality and Recovery" by Terri M. Walsh, Adhesive Age, December 1989. Similar viscometers are described in the references cited in said articles, as well as in U.S. Pat. Nos. 3,382,706; 3,710,614; 3,712,117; 3,762,429; 3,875,791; 4,299,199; 4,488,427; 4,566,181; 4,754,640; and 5,054,313.

The commercial use of vibratory viscometers of this type has been for the most part, in applications described in the foregoing references.

These prior art viscometers, however, are not suitable for applications utilizing high viscosity fluids, especially at high temperatures and pressures, such as the extrusion of plastic resins through dies to form various objects such as toys, wastebaskets and film.

Sensors are commercially available for measuring the temperature and pressure of resins in real time during the extrusion process; e.g. those manufactured by Dynisco, Four Commercial Street, Sharron, Ma. 02067 and Omega Engineering, Inc., One Omega Drive, Stamford, Conn. 06906.

However, no device for real time in-process measurement of high viscosity fluids at high temperatures and pressures has hitherto been available.

Because of the unavailability of such in-process high viscosity measurement equipment, it is necessary to monitor resin extrusion and similar manufacturing processes by obtaining a sample of the fluid and performing viscosity measurements on the sample. This is done by having part of the flow on its way through the extruder bypassed or extracted for measurement by one of the several commercially available viscometers especially designed for this purpose. Manufacturers of these on-line instruments include Seiscor Technologies, Tulsa, Ok. 74146; Rheometrics, Inc., Piscataway, N.J. 08854; and Gottfert Werkst Off-Prufmaschinen GmbH, Buchen, Germany.

A non-oscillating high viscosity viscometer[1] with a channel for fixed plate measurement is reported by McGill University Professor John M. Dealy in U.S. Pat. No. 4,571,989. Dealy says there are many reasons for being able to determine rheological properties of the molten plastic during processing of that material.
[1] True Shear Rheometer introduced May 1992, Interlaken Technology Corp., Eden Prarie, Minn. 55346.

The importance of knowing rheological properties such as fluid viscosity during the extrusion process cannot be overemphasized. The fact that many companies go to great expense to measure fluid viscosity on an offline basis bears out this contention. Measurement and control of the product directly in-line in real time while the process is occurring is very important in maintaining uniform quality of the extruded product. In an article in Food Extrusion Science and Technology, Marcel Dekker, Inc., N.Y. (1992) entitled "An On-Line Slit Rheometer for Measurement of Rheological Properties of Dough", C. G. Gogos and S. Bhakuni wrote the following regarding the current need for an extruder viscometer to overcome the shortcomings of measurement methods now in use:

"Obviously the viscosity function can be effectively used for monitoring product quality. In continuous food processing operations (e.g., dough extrusion), it can also be utilized for controlling the process.

On the other hand, the growing interest in automating food processing operations has generated an immediate need for real-time knowledge of rheological properties so that one can maintain tighter control of process conditions and thus product quality. Most of the approaches to such measurements have utilized one of the following methods:

Placing pressure transducers before the die: complex die geometries render this method approximate at best.

Using capillary or slit dies tapped on the processing equipment before the die: this allows a side waste dough stream to flow under the die pressure drop."

According to Dealy[2] a variety of high viscosity rheometers are commercially available. However, most of them are off-line instruments. The time required to obtain a result from these rheometers can vary from minutes to hours, depending on the complexity of the measurement. A lot of product is extruded while such viscosity measurements are being made, since it is not practical to turn the extruder off while making the measurements. With such viscometers being off-line and/or requiring a considerable amount of time to make viscosity measurements, adjustment of the composition and/or process parameters of the fluid in an effort to keep its viscosity within the desired tolerance limits, is often fruitless.
[2] U.S. Pat. NO. 4,571,989.

Off-line viscometers are very expensive. They require long signal delay. Efflux from the required side stream may constitute a waste problem. Major instrument components must be mounted near the process equipment.

Accordingly, an object of the present invention is to provide a transducer for a vibratory viscometer, having an improved rotary vibratory probe capable of directly and quickly performing inline measurements on high viscosity fluids at high temperature and pressure in real time; such performance not being hitherto within the capability of available transducers.

SUMMARY OF THE INVENTION

The vibratory viscometer transducer arrangement according to the present invention has a hollow sensor tip which is preferably small in length and radius, having a torsionally compliant sheath, the tip being driven by an inner shaft which is torsionally vibrated by a crossarm which is caused to oscillate by a driver coil and associated control circuitry, at a constant amplitude as measured by the output of a pickup coil. According to one aspect of the invention, the sensor tip is such that its moment of inertia about the axis of torsional oscillation is at least an order of magnitude less than the sum of the moments of inertia of the crossarm and shaft about that axis.

According to another aspect of the invention, the driver and pickup coils are oriented at right angles to each other with their axes substantially coplanar, so as to reduce cross-talk between the coils and to allow them to be more closely positioned to each other in a way which allows the size of the transducer housing which contains them to be reduced.

In use, the sensor tip is immersed in a fluid the viscosity of which is to be measured, and the viscous resistance presented by the fluid to the oscillatory motion of the surface of the sensor tip is determined and converted into a signal indicative of viscosity by an electronic control unit.

GENERAL DESCRIPTION

The high viscosity transducer of the present invention, which is an improvement over the transducer described in U.S. Pat. No. 3,382,706, [3] measures viscosity at high temperature and high pressure, and does not require creation of a wasteful sidestream.

[3] Two of the three inventors of the present invention were the inventors in U.S. Pat. No. 3,384,706.

In a preferred embodiment of the invention, a transducer for a vibratory viscometer has a rotary vibratory sensor tip or probe with an externally threaded cylindrical body portion for mounting directly into extruder barrels and extruder heads or die adapters, with the probe tip projecting directly into the plastic melt.

The transducer probe is sufficiently small so that it installs into standard threaded thermocouple and pressure gauge port wells which are provided on the extruder barrels of existing injection molding machines, so that no alteration of the machines is needed.

The transducer probe also can be used for measuring high viscosity at high pressures in various types of tanks and vessels.

The transducer of the present invention requires electronic control circuitry coupled to the drive and detector coils which cause the crossarm of the transducer to oscillate in the desired manner, i.e. so as to torsionally oscillate the sensor tip with a predetermined angular amplitude at the mechanical resonant frequency of the sensor tip and associated moving parts of the transducer.

An electronic control unit suitable for use with the transducer of the present invention is disclosed in U.S. Pat. Nos. 3,762,429 and 4,566,181. Other control circuits can be used which supply a drive current to the drive coil of the transducer such that the angular amplitude of oscillation of the crossarm (as measured by the amplitude of the signal generated by the detector coil) is maintained at a constant value, and the power supplied to the drive coil (which is a measure of the viscosity-density product of the fluid in which the tip is immersed) is determined.

The electromagnetically driven crossarm used in the transducer of the present invention is like those disclosed in patents mentioned above. Preferably, however, the crossarm is specially shaped as hereafter described. The novel shape of the crossarm of the transducer, best shown in FIG. 6, results in improved performance by decreasing cross-talk[4] and allowing the size of the transducer housing to be reduced. Small transducer size is important, since the transducer must be able to fit on an extruder adjacent to other equipment on and near the extruder.

[4] This is, magnetic coupling between the driver and detector coils.

An additional important difference from prior art transducers is that the moment of inertia of the sensor tip and its associated compliant sheath is extremely small[5] as compared with the moment of inertia of the cylinder and vibrating sphere sensors used in prior art vibratory viscometers.

[5] Exhibiting less than one-hundredth the moment of inertia.

In a typical prior art vibratory viscometer having a vibrating sphere sensor probe, the relatively high moment of inertia results in a two degree of freedom mode of vibration. Their modes are (i) in phase at approximately 650 Hz., and (ii) out of phase at approximately 1300 Hz.. Either mode may be used to measure viscosity. This dual mode vibration in a typical prior art vibratory sensor occurs because the moments of inertia of the crossarm and sphere are appreciable and the elasticity of the transducer shaft and sheath act together both (i) in-phase, where the combination of the crossarm shaft and sphere is the inertial element, and they twist in the same direction, and (ii) out-of-phase, where the crossarm and sphere twist in opposite directions.

In the transducer of the present invention, due to the low moment of inertia of the sensor tip, the mode of vibration is a simple harmonic motion with the cross arm and sheath shaft combination functioning as the vibratory elements and twisting in the same direction.

DETAILED DESCRIPTION

Figure 1:
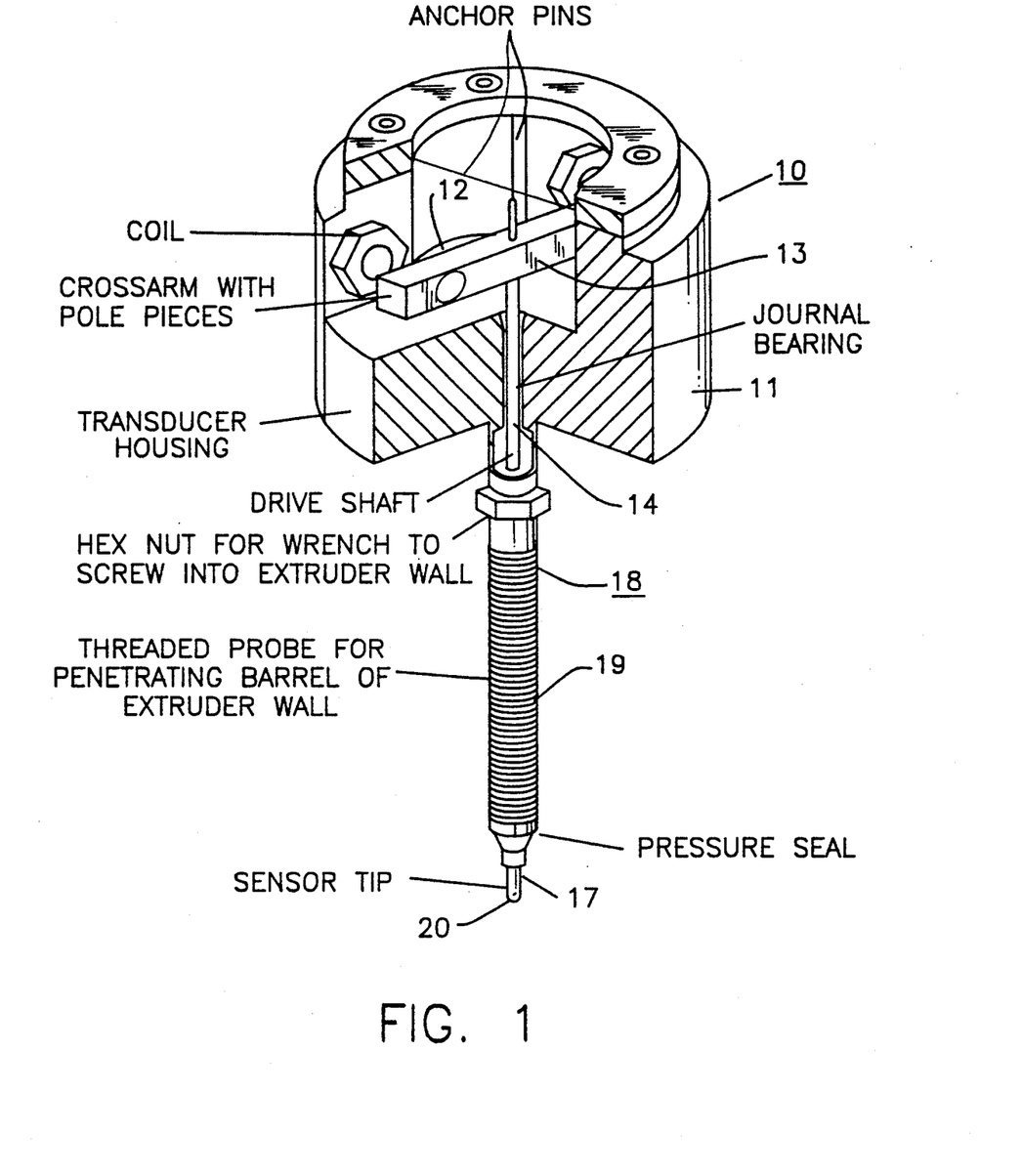
FIG. 1 is a partially cut away isometric view of a transducer with a vibratory rotary probe for the measurement of high viscosity at high temperature and high pressure, according to a preferred embodiment of the present invention.

The transducer 10 shown in FIG. 1 has an upper housing 11 containing an electromagnetic drive and pickup assembly 12, the operation of which is described in some detail in the patents previously identified.

Figure 6:
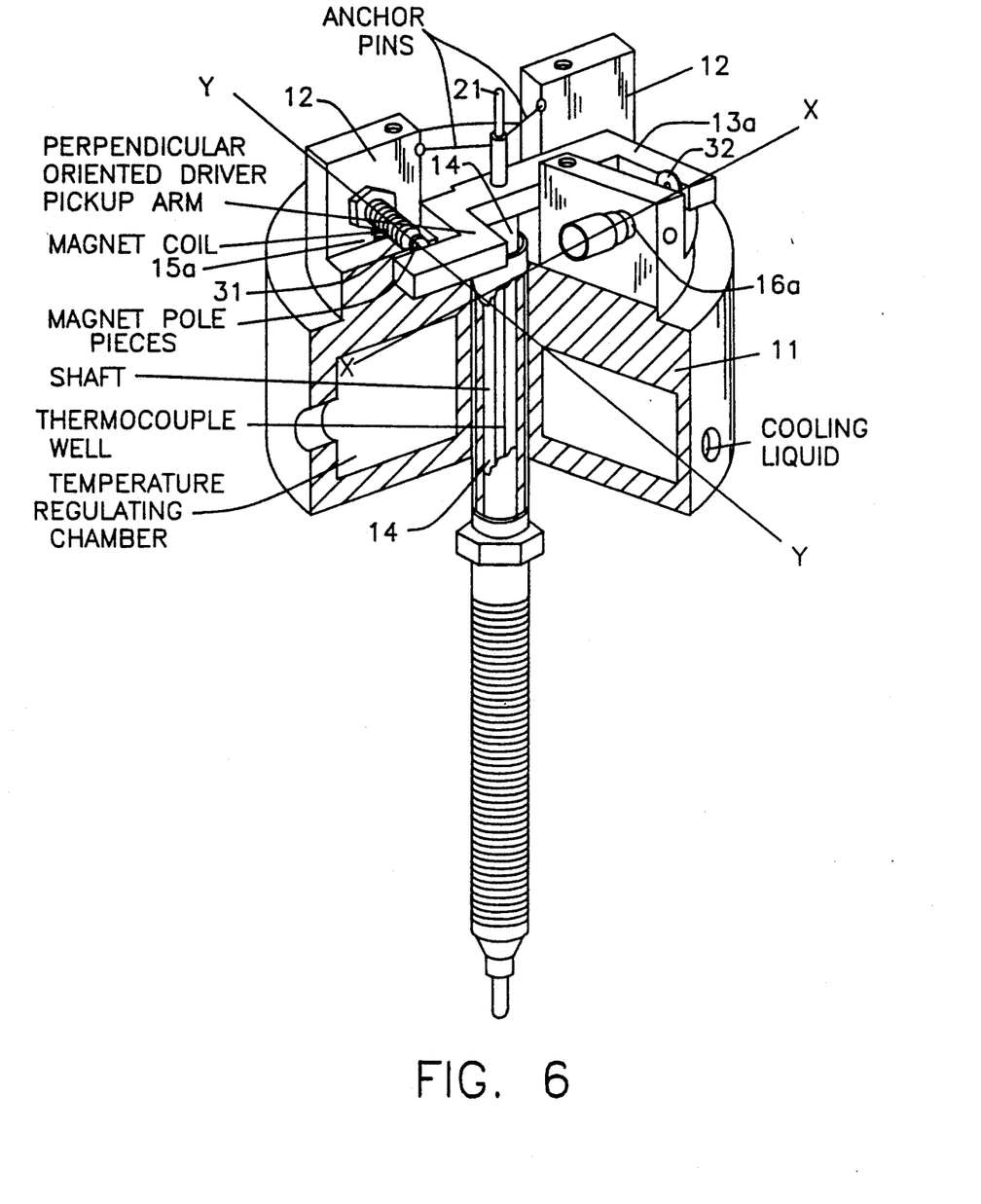
FIG. 6 is a partially cut away, partially isometric front elevation cross-sectional view through the driver and pickup portions of an alternative embodiment of the transducer shown in FIG. 1, showing the arrangement of the driver/pickup crossarm which vibrates to cause the sensor tip to torsionally oscillate, and the arrangement of the driver and detector coils which causes the crossarm to vibrate with a predetermined angular amplitude.

A modified and preferred form 12a of the assembly 12, as best seen in FIG. 6, has a magnetic crossarm 13 secured to the upper end of a drive shaft 14. An electromagnetic drive coil 15a causes the crossarm 13 to oscillate at a mechanical resonant frequency determined by the compliance, moment of inertia and other mechanical characteristics of the vibratory system comprising the crossarm 13, shaft 14, and the complaint sheath 17 which forms most of the outer surface of the sensor tip 20.

The electromagnetic detector coil 16a, which is oriented at right angles to the drive coil 15a, provides an output signal having a frequency equal to the frequency of oscillation of the crossarm 13, and an amplitude corresponding to the amplitude of angular oscillation of the crossarm.

Affixed to the housing 11 is the vibratory rotary probe 18 having an externally threaded body portion 19 with a ½", 20 pitch National Fine thread; the threading and exterior dimensions of the probe being the same as those of standard thermocouple and pressure probes designed to withstand the high temperature and high pressure of plastic extruders and to be mounted in the ports of extruders to accommodate thermocouples.

Figure 2:
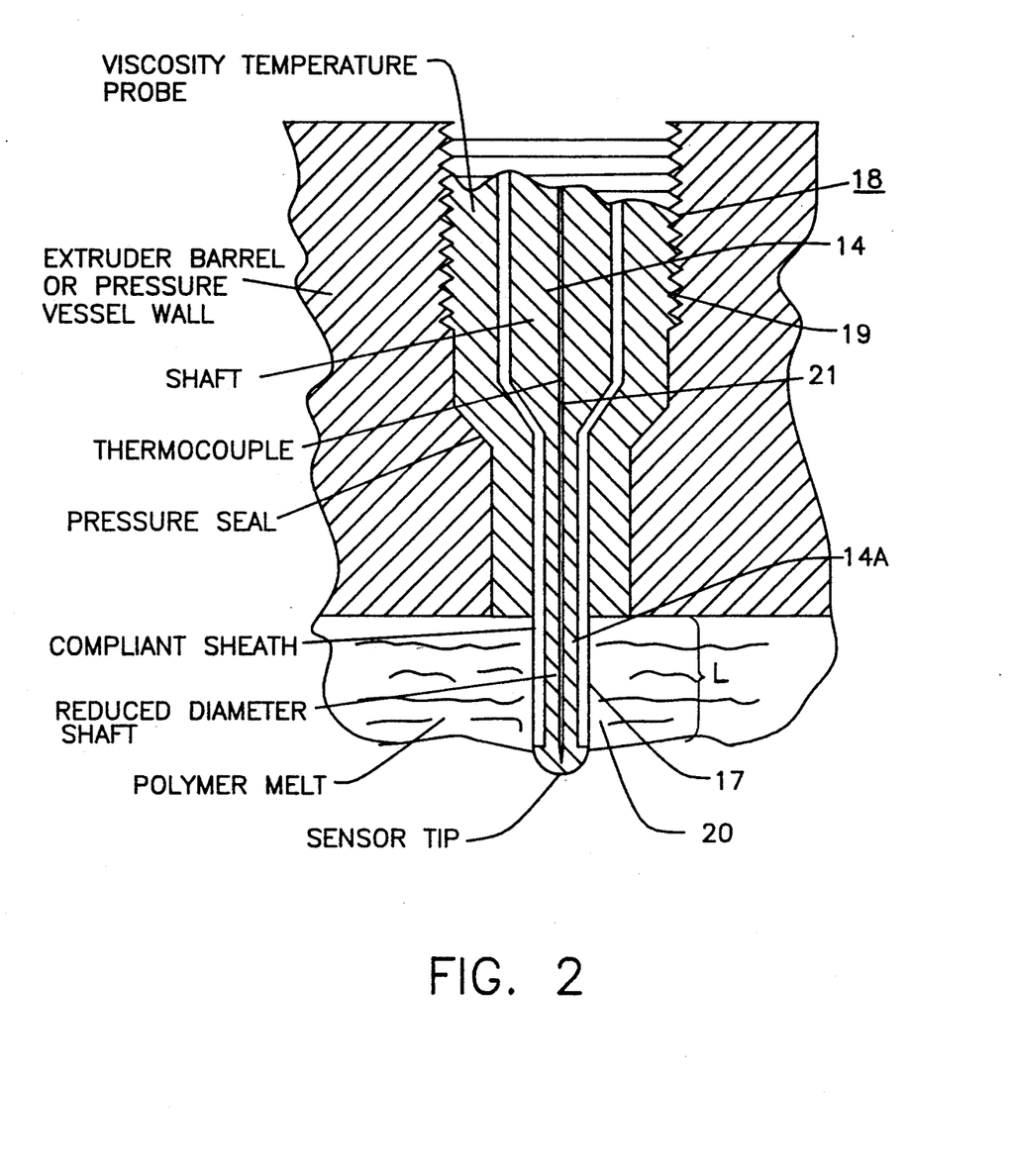
FIG. 2 is a cross sectional view showing the construction of the lower portion vibrating rotary probe of the transducer shown in FIG. 1.

The probe 18, best shown in FIG. 2, measures temperature as well as viscosity. The sensor tip 20 is very short, having a length L between the end of the tip 20 and the junction of the compliant sheath 17 with the end of the body portion 19 of the probe 18. The short length L of the sensor tip 20 serves to allow clearance for extruder screws and for any stirring mechanism in the pressurized vessels or tanks into which the tip 20 extends.

In FIG. 2 a thermocouple 21 extends inside the shaft 14 along the torsional rotary axis of the probe 18, to the tip 20 where it measures temperature. The torsionally compliant shaft 14 cooperates with the torsionally complaint sheath 17 to form an elastic structure which twists the tip 20 in torsional oscillation.

In the preferred embodiment the tip 20 has a length L of 0.50 inches (1.27 cm.), an outer diameter $D_o$ of 0.250 inches (0.635 cm.), a wall thickness[6] of 0.035 inches (0.089 cm.), and an inner diameter $D_i$ of 0.21 inches (0.53 cm.). The reduced diameter portion 14a of the shaft 14 inside the tip 20 has a diameter of 0.180 inches (0.46 cm.), which increases to a diameter of ¼ inch at a distance of one inch from the lower end of the probe body portion 19; the length L of the probe tip being 0.50 inches (1.27 cm.). The diameter of the central axial hole in the shaft 14 for receiving the thermocouple 21 is 0.062 inches (0.159 cm.).

[6] That is, the thickness of the compliant sheath 17.

The increased diameter of the upper part of the shaft 14 increases the torsional rigidity of the shaft and minimizes any tendency of the mechanical elements to twist excessively, while also minimizing any tendency of flexural vibrations to occur; thus improving performance of the viscometer and reducing sensitivity to factory vibrations. Anchor pins hold the shaft in an axial position and also minimize any tendency of the shaft to vibrate in a flexural mode.

The pressures utilized in extrusion, injection molding and blow molding processes extend over a very large range, from one to 30,000 psi, and much higher in some cases. Thus resistance to pressure-induced collapse becomes an important consideration when designing a transducer probe for such applications. The viscometer transducer of the present invention is capable of operating over such pressure ranges, provided that due care in design is taken to insure adequate resistance to pressure.

An equation[7] for the collapsing pressure P of the type 316 stainless steel thin-walled cylindrical tip is $$P = 60,000 \left[ \left(\frac{t}{D}\right) - \left(\frac{t}{D}\right)^2 \right] \quad (1)$$

where t is the wall thickness, and D is the outer diameter of the tube. For the model probe described above the collapsing pressure therefore is $$P = 60,000 \left[ \left(\frac{0.035}{0.250}\right) - \left(\frac{0.035}{0.250}\right)^2 \right] = 9.6 \times 10^3 \text{ psi} \quad (2)$$

a value which adequately covers an important part of the resin processing range for applications such as blow molding of polyethylene sheeting. The collapsing pressure calculated according to Equation 1 serves as a guide, it being prudent to set an intermittent working pressure much lower (3,000 psi in the case of the figures used in Equation 2).

[7] Information supplied by Joseph Smik, Superior Tube Company, Norristown Pa. 19404.

The resistance of the transducer probe tip to processing pressure can be increased by increasing the wall thickness of the compliant sheath and by turning the sheath from solid stock instead of using commercial tubing.

If excessive pressure collapses the sheath 17 (FIG. 2), the inner portion 14a of the shaft 14 prevents total collapse and minimizes the risk of actual rupture of the sheath wall, which becomes deformed by the excessive pressure.

As previously mentioned, inside the shaft 14 along the central longitudinal axis (of torsional oscillation) thereof, a hole is drilled for the thermocouple.

The tip 20 of the probe 18 is constrained to oscillate about the longitudinal axis of the shaft. The mechanical relationships between spring constants of the vibratory system, viscous resistance of fluid C and moments of inertia I's are diagrammed in FIG. 3.

Although the compliance $G = 0.84 \times 10^{12}$ dynes/cm² of stainless steel used for the sheath and shaft of the viscometer of the aforementioned embodiment of the present invention provides adequate performance, a stiffer shaft of higher modulus made of a material such as tungsten carbide ($G = 5 \times 10^{12}$ dynes/cm²) would be expected to provide even better performance, since twisting movement would be essentially confined to the sheath.

Figure 3:
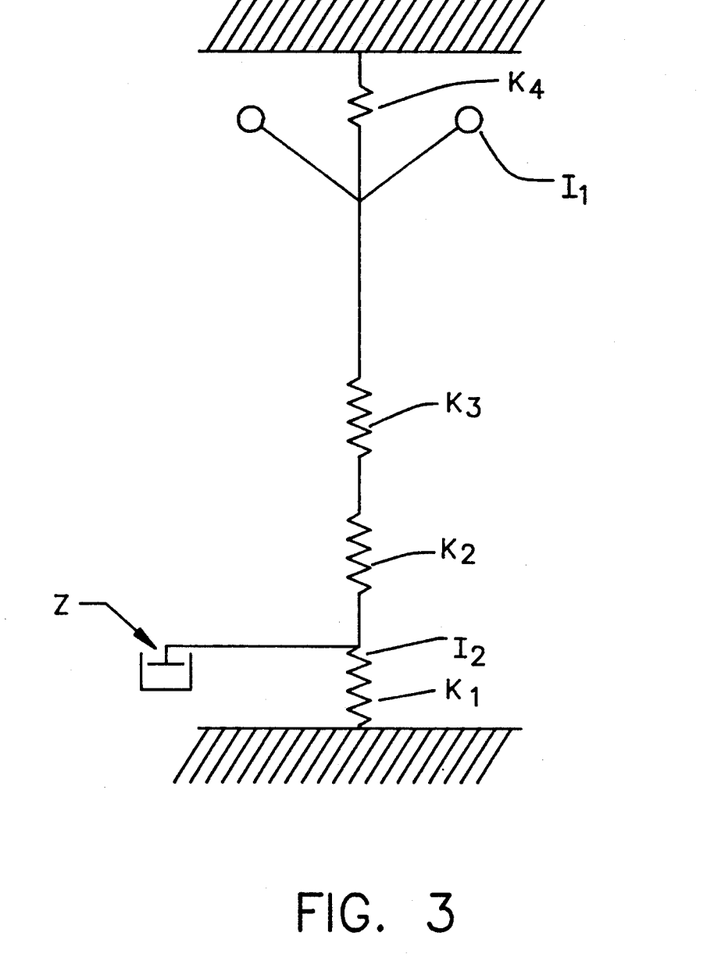
FIGS. 3 is a schematic diagrams showing the mechanical relationship of moving parts of the vibratory rotary probe of the transducer shown in FIG. 1.

In FIG. 3 the several vibratory elements of the high viscosity transducer of the present invention are schematically diagrammed; and the parameters $K_1$, $K_2$, $K_3$ and $K_4$ represent the spring constants of the transducer. $K_1$ is the spring constant of the sheath; $K_2$ and $K_3$ are the spring constants of the shaft and the crossarm affixed thereto; and $K_4$ is the spring constant of the anchor pins. The composite spring constant K for the transducer may be determined from the relationship:

$$K = \frac{K_2 K_3 K_4 + K_1 K_3 K_4 + K_1 K_2 K_4 + K_1 K_2 K_3}{K_1 K_2 K_3 K_4} \quad (3)$$

In FIG. 3 $I_1$ is the combined moment of inertia of the crossarm and shaft, while $I_2$ is the moment of inertia of the sensor tip; with $I_2$ being much less than $I_1$—preferably no more than one-hundredth of $I_1$. Z represents the viscous loss experienced by the oscillating sensor tip.

The transducer shown in FIG. 1 had a sharp mechanical resonance in air at 278.4 Hz., with a quality factor $Q^{-1} = 1.32 \times 10^{-3}$. It behaved like a classical single degree of freedom vibrating system, where $$I\phi'' + Z\phi' + K\phi = S \quad (4)$$

in which:

S is the driving torque applied to the crossarm 13;
I is the combined moment of inertia of the shaft, crossarm and sensor tip with respect to the axis of the shaft 14;
$\phi$ is the angular amplitude of oscillation of the crossarm and $\phi'$ and $\phi''$ are its first and second time derivatives;
Z is the torsional impedance, given (for a purely viscous liquid) by $$Z = \sqrt{\pi \eta f \rho} \quad (5)$$

where:

$\eta$ is the viscosity in poise;
f is the mechanical resonant frequency; and
$\rho$ is the density of the fluid.

For a single degree of freedom system, $$f = (1/2\pi)\sqrt{K/I} \quad (6)$$

yielding a resonant frequency of 261 Hz. for the embodiment shown in FIG. 1, and a resonant frequency of 262.5 Hertz with a quality factor $Q^{-1}$ of $6.66 \times 10^{-4}$ for the embodiment shown in FIG. 6 wherein the crossarm 13a is shaped to enable the driver and detector coils 15a and 16a to be oriented at right angles to each other.

For the embodiment shown in FIG. 1 and according to Equation 6, $I = 2.41 \times 10^8$ dynes/cm/$(2\pi 278$ sec$^{-1})^2 = 79$ gm. cm.$^2$.

The moment of inertia I of the end of the sensor tip where motion of the sheath is a maximum, is determined as $$I = \frac{mr^2}{2} = \frac{\pi r^2 l \rho}{2} \quad (7)$$

where m is the mass of the sensor tip;
r is the radius of the sensor tip;
l is the length of the sensor tip; and
$\rho$ is the density of the sensor tip.

The applicable parameters for the models of the preferred embodiments shown in FIGS. 1 and 6 which were tested are shown in Table I.

TABLE I

| Embodiment | Sensor Radius r | Sensor Length l | Sensor Moment of Inertia |
|---|---|---|---|
| FIG. 1 | 0.238 cm. | 0.20 cm. | 0.16 gm/cm$^2$ |
| FIG. 6 | 0.318 cm. | 0.20 cm. | 0.29 gm/cm$^2$ |

The ratio of shaft/crossarm combined moment of inertia to sensor tip moment of inertia was 494:1 for the FIG. embodiment and 272:1 for the FIG. 6 embodiment.

Figure 4:
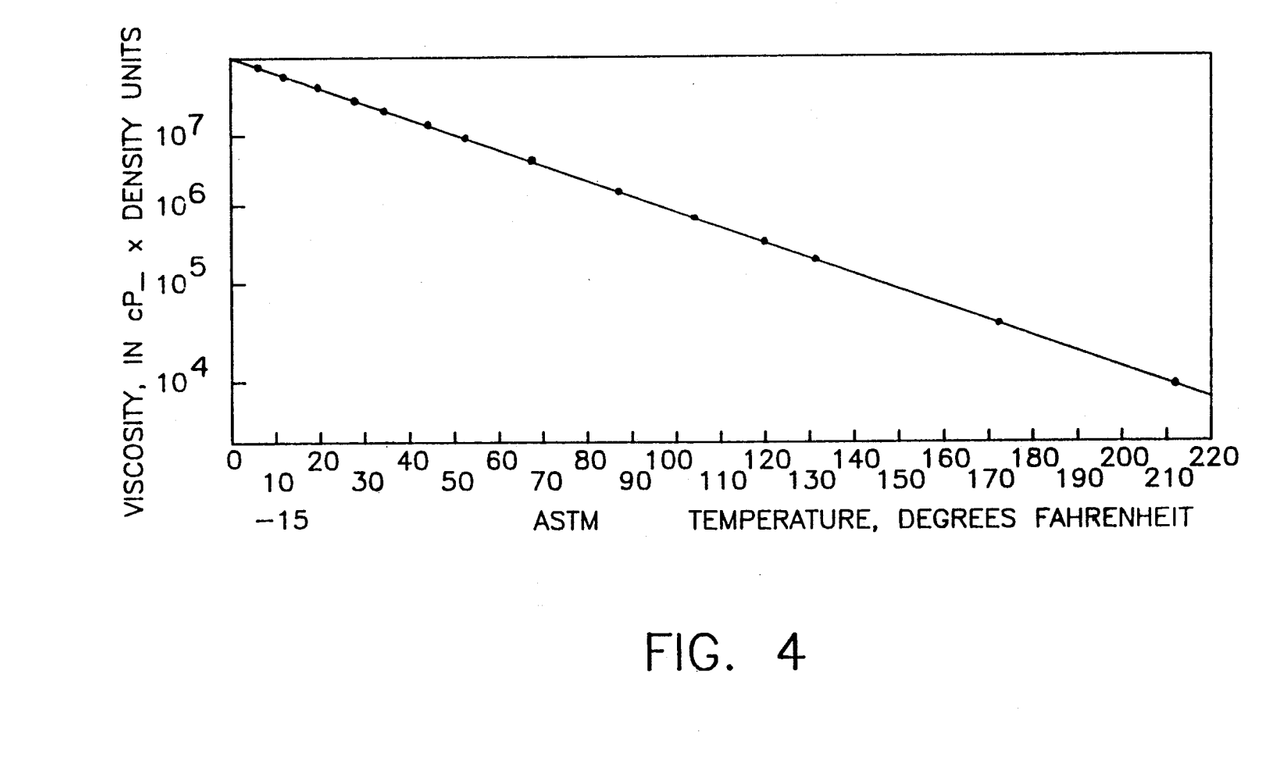
FIG. 4 is a calibration chart for the viscometer transducer shown in FIG. 1, showing the variation of the ratio of measured viscosity to true viscosity over the range of $10^4$ to $10^8$ centipoise.

Calibration of each viscometer was accomplished by immersion of the tip 20 in a Cannon Standard liquid of precisely known viscosity, and setting the instrument viscosity points at different temperatures over the range $10^4$ to $10^8$ centipoise density (gm/cm$^3$) units, as shown in FIG. 4. After calibration, the transducer shown in FIG. 1 as well as the alternative embodiment shown in FIG. 6 were used successfully to measure the viscosities of other standard fluids, including fluids of high viscosity. This procedure demonstrated the capability of the transducer to measure high viscosities accurately.

Since the vibratory method of viscosity determination actually measured viscosity-density product, a correction must be made if the fluid density is significantly different from 1 gm./cm.$^3$ [8]. This correction is usually done automatically by an adjustment in the electronic control unit 33 (FIG. 7), provided that the fluid density is known, either by use of an assumed value or by an actual density measurement.

[8] The density of water is 1 gm./cm.$^3$. The viscosity of water is 1 centipoise.

Figure 5:
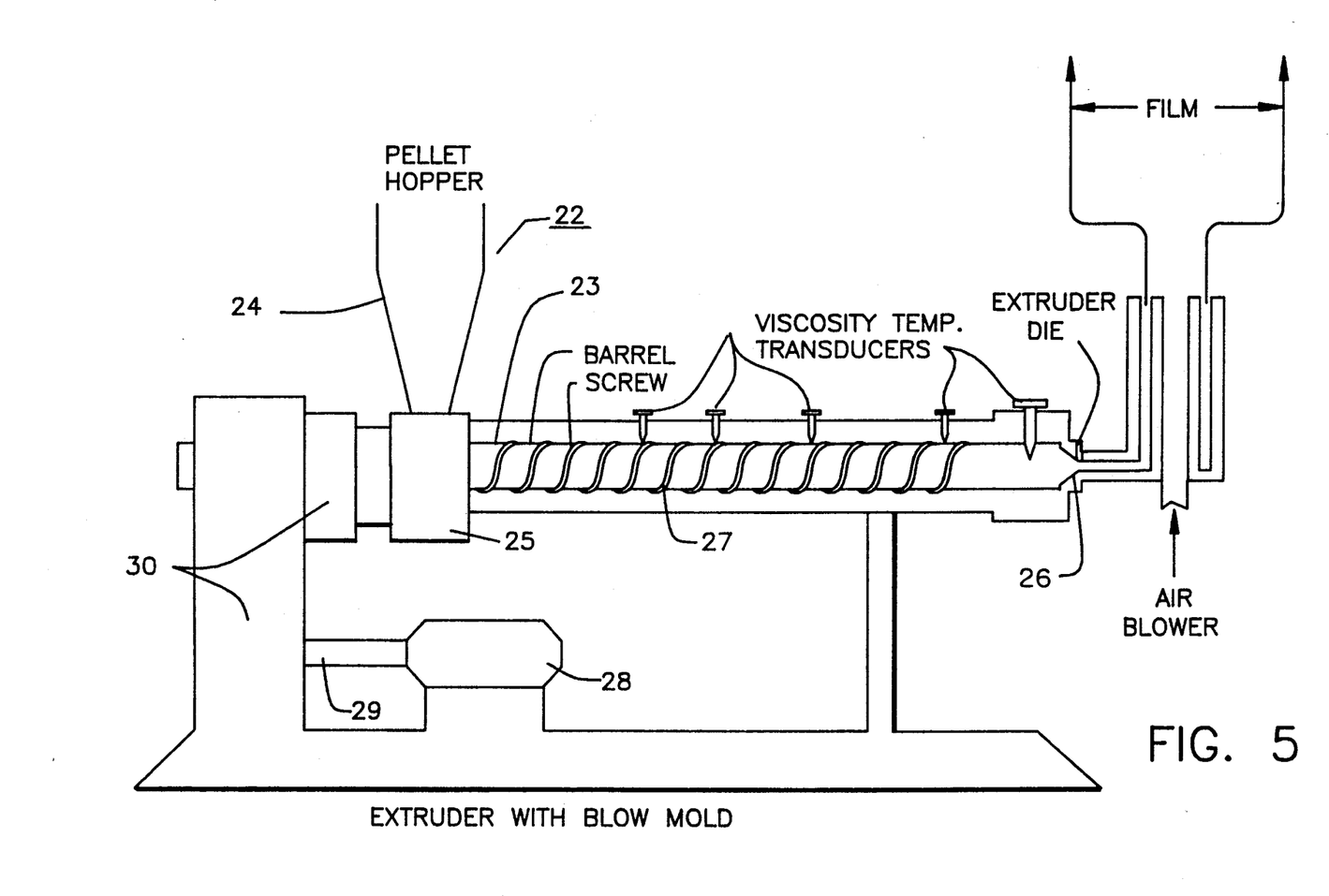
FIG. 5 is a partially cut away side elevation view of machinery for extruding molten plastic resin into a film, showing locations for insertion of the vibratory rotary probe of the transducer shown in FIG. 1, into the resin stream for in-line measurement purposes.

In a field test the transducer (the embodiment shown in FIG. 1) was plugged into the extruder die 23 of a commercial extruder 22 as shown in FIG. 5. This commercial extruder was being used to produce polyethylene film.

In the extruder 22, pellets of the resin are dumped into the hopper 24 and melted into molten polymer by pressure generated by the revolving screw 27 of the extruder, which moves the resin from the hopper-fed chamber 25 to the extruder die 26. The screw 27 is driven by a motor 28 via a motor shaft 29 and transmission means 30.

The pressure of the molten polymer is measured by a separate probe (not shown); which pressure was 2,180 psi when the test was conducted. The molten polymer temperature, also measured by a separate probe (not shown), was 375° F. (190° C.) when the extruder screw 27 was rotating at 80 revolutions per minute.

Areas on the barrel and die of an extruder where viscosity needs to be measured are sometimes cluttered with temperature and pressure probes. Thus space is at a premium, even though the present invention enables both viscosity and temperature to be measured via a single threaded extruder access well.

In the embodiment shown in FIG. 1 the generally cylindrical transducer housing 11 was made with an outer diameter of 4½ inches and a height of 2⅝ inches; while the alternative embodiment shown in FIG. 6 permitted a significant reduction of the housing diameter to three inches, while the housing height was reduced to 2⅛ inches.

An important feature of the alternative embodiment shown in FIG. 6 is that in order to reduce troublesome magnetic cross-talk between the driver and detector pickup coils, the crossarm 13 of FIG. 1 is replaced by a crossarm 13a having one end configured to support a pole piece 31 oriented to interact with a driver coil 15a having an axis y—y; while the other end of the crossarm 13a has an end configured to support a pole piece 32 oriented to interact with a pickup coil 16a having an axis X—X, at right angles to axis y—y. While it is preferred that axes y—y and X—X be coplanar for stability, they do not necessarily have to be coplanar.

The vibratory method for determination of rheological properties (such as viscous loss, elastic component of complex viscosity, and complex viscosity) disclosed in U.S. Pat. No. 4,754,640 is applicable to the high viscosity, high temperature viscometer of the present invention. This method requires that mechanical oscillation frequencies be measured.

In one experiment using the viscometer of the present inventions to determine the variation of mechanical resonant frequency of the transducer 10 (in air) with temperature, from 0° C. to 80° C. the resonant frequency dropped linearly from 285.0 Hz. to 281.5 Hz. In air at room temperature the resonant frequency was 279.20 Hz. In a standard high viscosity liquid of 8,750 centipoise the resonant frequency was 274.16 Hz. at room temperature.
[9] The embodiment shown in FIG. 1.

Despite its small area of contact with fluids, the small sensor tip 20 was found to detect viscosity with good quantitative accuracy.

Standard threaded wells or ports to receive pressure and temperature gauges have been incorporated in the thick walls of extruders for many years. However, until the present invention it has not been proposed, or even practical, to use the wells to measure the viscosity of the high pressure, high viscosity fluid comprising the material being extruded.

In addition to its capability of determining viscosity over a wide viscosity range as shown in FIG. 4, in the extruder application the sensor of the present invention was also responsive to fluid pressure and the rotational speed of the extruder screw when the sheath wall surface area was too small. The hydrostatic pressure effect on polymer melt viscosity must be allowed for at high pressures, in accordance with experimental results and formulas disclosed by Bryce Maxwell and Alex Jung in the article which appeared in Modern Plastics, November 1975, and also in Effect of Pressure on Viscosity, TS Report GTSR 54 by P. J. Brower, Amoco Chemicals Co.

For viscosity measurements performed utilizing the transducer of the present invention (the embodiment shown in FIGS. 1 and 2), at pressures of 100 to 2,500 psi the reproducible pressure-induced increase in viscosity for polyethylene was less than 2%.

Values of the apparent viscosity measured (by the transducer embodiment of FIG. 1) in an extruder for a polyethylene melt (having a melt index MI of 2.2) increased as follows due to the effect of pressure and extruder screw rotational speed[10] on the sensor. These results proved to be reproducible, so that it is feasible to have the electronic control unit 33 of the viscometer make appropriate correction of the viscosity reading, when provided with data as to fluid pressure and extruder screw rotational speed.
[10] Extruder screw rotational speed corresponds to flow rate of the fluid being extruded.

TABLE II

| True Viscosity (poise) | Apparent Viscosity (poise) | Extruder Screw Rotational Speed (rpm) | Fluid Pressure (psi) |
|---|---|---|---|
| 20 × 10⁵ | 30,000 | 40 | 1,620 |
| 20 × 10⁵ | 90,000 | 70 | 2,000 |
| 20 × 10⁵ | 150,000 | 95 | 2,500 |
| Sensor crushed | | 98 | 2,700 |

By manual or electronic correction of the apparent viscosity for the effects of pressure and flow rate (i.e. extruder screw rotational speed) utilizing data similar to that shown in Table 1, the true viscosity is determined.

For the embodiment of FIG. 6 the sheath wall thickness was increased over that of the FIG. 1 embodiment, by increasing the outer diameter of the sheath from 0.18 inches (0.457 cm.) to 0.250 inches (0.635 cm.). The collapse pressure as determined by Equation 1 above is 9,600 psi. Using a laboratory pressure generator [11] the results set forth in Table III were obtained for the effect of pressure on viscosity as determined with the arrangement shown in FIG. 7.
[11] Manufactured by Advanced Pressure Products, Cornell University Research Part, Ithaca, N.Y. 14850-1298.

TABLE III

| True Viscosity (centipoise) | Fluid Pressure (psi) |
|---|---|
| 2.92 × 10⁶ | 50 |
| 2.90 × 10⁶ | 500 |
| 2.88 × 10⁶ | 1,000 |
| 2.98 × 10⁶ | 1,500 |
| 2.98 × 10⁶ | 3,000 |
| 3.20 × 10⁶ | 3,500 |
| 3.20 × 10⁶ | 4,800 |

These viscosity results were obtained on repeated application of pressure. It was not clear whether the increase in viscosity readout above 3,000 psi was due to elastic deformation of the sensor tip or to a shift of the zero calibration of the viscometer.

A further correction is electronically made to the viscosity because of its dependence on the fluid temperature T in accordance with the Arrhenius equation $$\eta = \eta_{oe} k/T \qquad (8)$$

where $\eta_{oe}$ is the measured viscosity of the fluid at temperature T;

$\eta$ is the temperature-corrected viscosity of the fluid at temperature T; and k is the Boltzmann constant.

Figure 7:
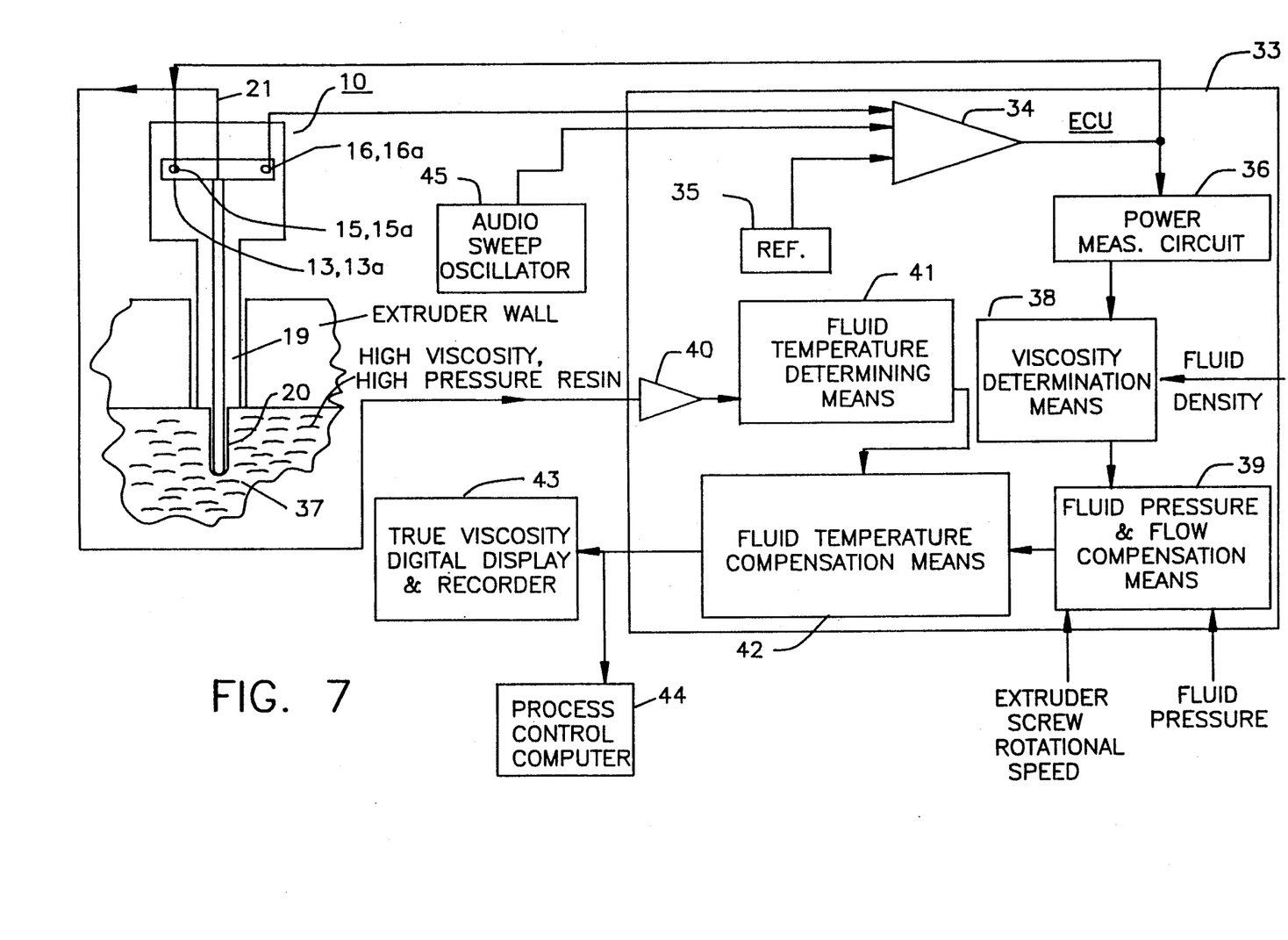
FIG. 7 is a functional block diagram showing the operation of the transducer of FIG. 1 as well as the alternative embodiment thereof shown in FIG. 6, in conjunction with the associated electronic control unit and display/recorder.

Both temperature T and viscosity are measured by the transducer 10 and its associated electronic control unit 33 (FIG. 7).

The preferred embodiment of this invention is a combination high viscosity and high temperature measuring transducer. A hollow tip 21 small in length and radius, having a torsionally compliant sheath 17, is immersed in the fluid being measured. The tip 21 is driven by a compliant inner shaft 14 that is torsionally vibrated by a crossarm 13 or 13a, which is caused to oscillate by a driver coil 15 or 15a at a constant amplitude as measured by the output of a pickup coil 16 or 16a; the driver and pickup coils preferably being oriented at right angles to each other with their axes substantially coplanar.

Viscous resistance presented by the fluid to the oscillatory motion of the surface of the sensor tip is detected and converted into viscosity by an electronic control unit 33.

The overall operation of the transducer 10 and its associated electronic control unit 33 is shown by the functional block diagram of FIG. 7.

In the electronic control unit 33, a gain-controllable amplifier 34 has an input terminal connected to the output of detector coil 16 or 16a, and an output terminal connected to supply a drive signal to corresponding driver coil 15 or 15a, in a positive feedback loop which causes the crossarm 13 or 13a to oscillate at the mechanical resonant frequency of the crossarm/shaft/sheath/tip vibratory system of the transducer 10.

The amplifier 34 compares the angular amplitude of mechanical oscillation as measured by the amplitude of the signal from the detector coil 16 or 16a, to a reference value from the reference source 35, and the resulting difference signal varies the gain of the amplifier 34 so as to maintain a constant amplitude of mechanical oscillation.

The drive current which is provided to the driver coil 15 or 15a by the amplifier 34 is sampled by a power measuring circuit 36 to determine the amount of power required to maintain a predetermined (by the reference 35) amplitude of mechanical oscillation when the transducer tip 20 is immersed in a high viscosity fluid 37, the viscosity of which is to be measured. The resulting output signal of the circuit 36 has a value corresponding to apparent viscosity-density product.

A viscosity determination means 38 divides the apparent viscosity-density product signal from the power measuring circuit 36 by the fluid density, to convert said signal to an apparent viscosity signal. The fluid density data required for this conversion may be (i) assumed by the viscosity determination means, i.e. by providing a fixed value therefor, (ii) manually input by means of a keyboard, dial or the like, or (iii) provided by an inline or other densitometer (not shown) which actually measured the fluid density.

The apparent viscosity signal from the viscosity determination means 38 is corrected for the effects of fluid flow rate (as measured by extruder screw rotational speed) and fluid pressure at the fluid pressure and flow compensation means 39, to effect correction in the manner previously described, so as to provide a true viscosity output signal which, however, may still require temperature correction.

The output of the thermocouple 21 (which is incorporated in the transducer 10 as previously described) is received by a thermocouple amplifier 40. A fluid temperature determining means 41 converts the output of thermocouple amplifier 40 to a fluid temperature signal.

A fluid temperature compensation means 42 temperature-corrects the true viscosity signal from the fluid pressure and flow compensation means 39, utilizing the temperature signal from the fluid temperature determining means 41.

The output signal from the fluid temperature compensation means 42, corresponding to temperature-corrected true viscosity of the fluid 37, is coupled to a digital display and recorder 43, and to a process control computer 44 which may utilize this viscosity information to control the extruder or to generate a warning signal when the viscosity of the fluid being extruded falls outside a range deemed to be acceptable.

The transducer and associated circuitry described above are not limited to operation at the mechanical resonant frequency of the transducer; but may also be operated in a mode wherein the drive coil is supplied with a frequency-modulated alternating current signal which varies in frequency (at a relatively slow rate, preferably no more than two Hz.) over a range which preferably includes the mechanical resonant frequency of the transducer. The resulting spectra yield valuable information as to fluid properties.

Figure 8:
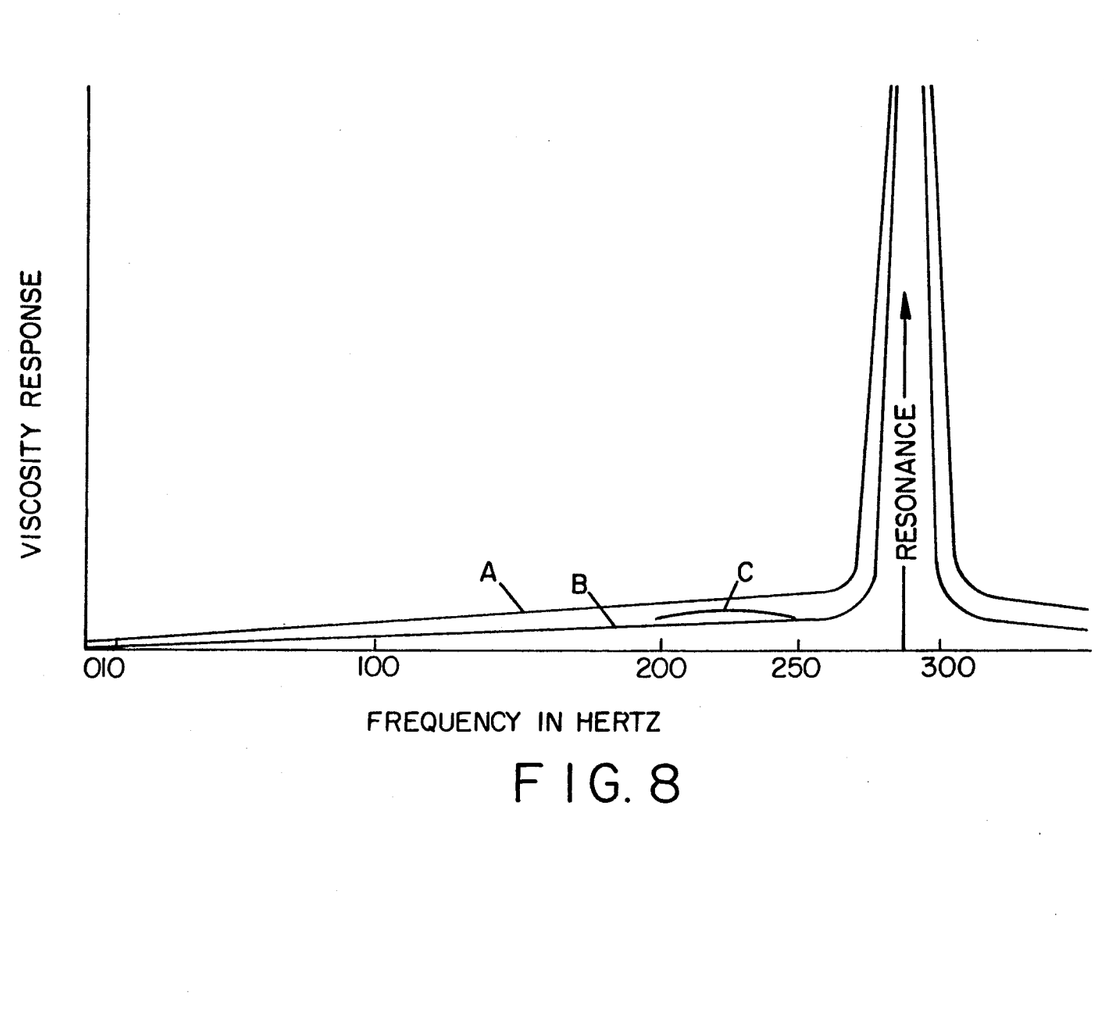
FIG. 8 is a graph of the pickup signal strength vs. mechanical vibration frequency response obtained with the transducers of FIGS. 1 and 6.

As shown in FIG. 8, off-resonant spectra for standard liquids of $10^5$ and $10^6$ centipoise are used for calibration using the high viscosity transducer of the present invention to determine the viscous loss for an unknown liquid C, continuously or at any frequency in the range of 200 to 250 Hz.

An audio oscillator 45 with continuous sweep, or an Acoustic Spectrometer[12], can be used to supply the drive coil 15a (FIG. 6) with an appropriate frequency modulated signal for this purpose. Automatic repeated sweeping from 10 to 100 Hz. on a resin production line yields data which may be converted to shear rate in radians/sec. according to a formula developed by John D. Ferry.[13]

[12] Available from Nametre Company (the assignee of this application), 101 Ferrese Street, Metuchen, N.Y. 08840.
[13] Oscillation Viscometey—Effects of Shear Rate and Frequency, John D. Ferry, Measurements and Control, Sept–Oct 1977.

It will be understood that the above described embodiments are for purposes of illustration only and that changes and modifications may be made thereto without departing from the spirit and scope of the invention.

We claim:

1. A transducer for a vibratory viscometer, comprising:

a housing;

a hollow body portion extending from said housing, the interior of the body portion communicating with the interior of the housing;

a compliant sheath extending from an end of said body portion remote from said housing and forming a sensor tip for immersion in a fluid;

a shaft having a longitudinal axis and extending from the interior of said housing through said body portion and into said sheath, said shaft being coaxial with said sheath, the end of said shaft remote from said housing being secured to the end of said sheath remote from said body portion, said shaft having a relatively small diameter minor portion disposed within said sensor tip and a relatively large diameter major portion disposed within said body portion;

a crossarm disposed within said housing and having a central portion secured to said shaft;

drive means comprising an electromagnetic driver coil for generating a magnetic field concentrated along a driver coil axis thereof, said drive means being operatively associated with said crossarm for vibrating said crossarm to torsionally oscillate said shaft and sensor tip about said longitudinal axis; and pickup means operatively associated with said crossarm for detecting the vibration thereof, said pickup means comprising an electromagnetic detector coil sensitive to varying magnetic fields oriented along a detector coil axis thereof, said driver coil and detector coil being disposed on opposite sides of said shaft and oriented so that said drive coil axis and said detector coil axis are at substantially right angles to each other.

2. The transducer according to claim 1, wherein said driver coil axis and said detector coil axis are substantially coplanar.

3. The transducer according to claim 1, wherein a part of said crossarm disposed on one side of said shaft is L-shaped, and a part of said crossarm disposed on the other side of said shaft has a shoulder part, said driver coil being disposed adjacent one of said parts and said detector coil being disposed adjacent the other of said parts, thereby enabling the housing to be reduced in size as compared to a housing containing a crossarm lacking such parts.

4. The transducer according to claim 1, wherein said shaft has a relatively small diameter minor portion disposed within said sensor tip and a relatively large diameter major portion disposed within said body portion.

5. The transducer according to claim 1, further comprising a thermocouple disposed within said sensor tip and having a lead extending into the interior of said housing through a hole in said shaft along the longitudinal axis thereof.

6. The transducer according to claim 1, wherein said shaft is torsionally compliant.

7. The combination according to claim 6, further comprising temperature measuring means for determining the temperature of said fluid, and fluid temperature compensation means for correcting said signal indicative of the viscosity of said fluid to reflect the effects of temperature.

8. The combination according to claim 7, wherein said temperature measuring means comprises a thermocouple disposed within said sensor tip and having a lead extending into the interior of said housing through a hole in said shaft along the longitudinal axis thereof, an amplifier coupled to said lead, and fluid temperature determining means coupled to said amplifier.

9. The transducer according to claim 1, wherein said shaft is relatively rigid with respect to said sheath.

10. The transducer according to claim 1, in combination with an electronic control means comprising:
    means coupled to said drive means and said pickup means for supplying power to said drive means to torsionally oscillate said shaft and sensor tip about said longitudinal axis with a constant angular amplitude;
    power measuring means for determining the amount of power supplied to said drive means and generating a corresponding power signal indicative of the apparent viscosity-density product of a fluid in which said sensor tip may be immersed;
    viscosity determination means for converting said power signal to a signal indicative of the viscosity of said fluid; and
    fluid pressure and flow compensation means responsive to data indicative of the rate of flow and pressure of said fluid, for correcting said signal indicative of the viscosity of said fluid, to reflect the effects of fluid flow and pressure.

11. A transducer for a vibratory viscometer, comprising:
    a housing;
    a hollow body portion extending from said housing, the interior of the body portion communicating with the interior of the housing;
    a compliant sheath extending from an end of said body portion remote from said housing and forming a cylindrical sensor tip for immersion in a fluid;
    a compliant shaft having a longitudinal axis and extending from the interior of said housing through said body portion and into said sheath, said shaft being coaxial with said sheath, the end of said shaft remote from said housing being secured to the end of said sheath remote from said body portion, said shaft having a relatively small diameter minor portion disposed within said sensor tip and a relatively large diameter major portion disposed within said body portion;
    a crossarm disposed within said housing and having a central portion secured to said shaft;
    drive means operatively associated with said crossarm for vibrating said crossarm to torsionally oscillate said shaft and sensor tip about said longitudinal axis; and
    pickup means operatively associated with said crossarm for detecting the vibration thereof,
    said crossarm, shaft and sensor tip comprising a mechanical oscillatory system wherein the moment of inertia of said sensor tip about said longitudinal axis is less than one-hundredth of the sum of the moments of inertia of said crossarm and said shaft about said axis, thereby substantially reducing susceptibility of said oscillatory system to undesirable modes of vibration when said sensor tip may be immersed in highly viscous fluids.

12. The transducer according to claim 11, wherein at least a part of said body portion is cylindrical and is externally threaded.

13. The transducer according to claim 1, or 11, wherein the length of said sensor tip as measured along said longitudinal axis is substantially less than the length of said body portion as measured along said longitudinal axis.

14. The transducer according to claim 1, or 11, further comprising means for providing a frequency modulated audio frequency signal to said drive means to cause said sensor tip to mechanically oscillate over a spectrum of frequencies extending outside the mechanical resonant frequency range of the transducer, so that said transducer may determine the viscosity of said fluid as a function of shear rate.

15. A transducer for a vibratory viscometer, comprising:
    a housing:
    a hollow body portion extending from said housing, the interior of the body portion communicating with the interior of the housing;
    a compliant sheath extending from an end of said body portion remote from said housing and forming a generally cylindrical sensor tip for immersion in a fluid;
    a shaft having a longitudinal axis and extending from the interior of said housing through said body portion and into said sheath, said shaft being coaxial with said sheath, the end of said shaft remote from said housing being secured to the end of said sheath remote from said body portion, said shaft having a relatively small diameter minor portion disposed within said sensor tip and a relatively large diameter major portion disposed within said body portion;
    a crossarm disposed within said housing and having a central portion secured to said shaft;

drive means operatively associated with said crossarm for vibrating said crossarm to torsionally oscillate said shaft and sensor tip about said longitudinal axis; and pickup means operatively associated with said crossarm for detecting the torsional vibration thereof, said crossarm, shaft and sensor tip comprising a mechanical oscillatory system wherein the moment of inertia of said sensor tip about said longitudinal axis is at least an order of magnitude less than the sum of the moments of inertia of said crossarm and the portion of said shaft outside said sensor tip about said axis, thereby substantially reducing susceptibility of said oscillatory system to undesirable modes of vibration when said sensor tip may be immersed in highly viscous fluids.

* * * * *